United States Patent
Karl

(10) Patent No.: US 8,760,971 B2
(45) Date of Patent: Jun. 24, 2014

(54) METHOD FOR CONTROLLING AN ULTRASONIC SENSOR AND ULTRASONIC SENSOR

(75) Inventor: Matthias Karl, Ettlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/641,260

(22) PCT Filed: Apr. 12, 2011

(86) PCT No.: PCT/EP2011/055714
§ 371 (c)(1),
(2), (4) Date: Dec. 21, 2012

(87) PCT Pub. No.: WO2011/141255
PCT Pub. Date: Nov. 17, 2011

(65) Prior Publication Data
US 2013/0100776 A1    Apr. 25, 2013

(30) Foreign Application Priority Data
Apr. 15, 2010    (DE) .......................... 10 2010 027 780

(51) Int. Cl.
G01S 3/80    (2006.01)
H04B 1/02    (2006.01)
G01S 1/74    (2006.01)

(52) U.S. Cl.
CPC ....................................... *G01S 1/74* (2013.01)
USPC .......................................... 367/137; 367/118

(58) Field of Classification Search
USPC ........................................................ 367/118
See application file for complete search history.

(56) References Cited

U.S. PATENT DOCUMENTS

| | | | |
|---|---|---|---|
| 5,339,290 | A | 8/1994 | Greenstein |
| 5,811,910 | A | 9/1998 | Cameron et al. |
| 6,617,765 | B1 | 9/2003 | Lagier et al. |
| 6,720,709 | B2 | 4/2004 | Porat et al. |
| 6,958,255 | B2 | 10/2005 | Kuri-Yakub et al. |
| 2003/0006673 | A1* | 1/2003 | Porat et al. ..................... 310/324 |

(Continued)

FOREIGN PATENT DOCUMENTS

| | | |
|---|---|---|
| DE | 101 39 341 | 2/2002 |
| DE | 103 46 620 | 5/2005 |

(Continued)

OTHER PUBLICATIONS

International Search Report for PCT/EP2011/055714, dated May 18, 2012.

(Continued)

*Primary Examiner* — Isam Alsomiri
*Assistant Examiner* — James Hulka
(74) *Attorney, Agent, or Firm* — Kenyon & Kenyon LLP

(57) ABSTRACT

An ultrasonic sensor has: a diaphragm that includes at least two partial regions for emitting and/or receiving ultrasonic signals, the two partial regions possessing different resonance characteristics; and at least one electromechanical transducer coupled to the diaphragm, to which transducer a control signal having at least two different control signal frequencies is applied. In this context, a first control signal frequency is in the range of a resonant frequency of a first partial region of the diaphragm, and a second control signal frequency is in the range of a resonant frequency of a second partial region of the diaphragm. Alternatively, two electromechanical transducers are used, which are coupled to a diaphragm and have different resonance characteristics.

9 Claims, 5 Drawing Sheets

(56) References Cited

U.S. PATENT DOCUMENTS

| | | | |
|---|---|---|---|
| 2004/0085858 A1* | 5/2004 | Khuri-Yakub et al. | 367/181 |
| 2005/0177045 A1* | 8/2005 | Degertekin et al. | 600/457 |
| 2007/0041273 A1* | 2/2007 | Shertukde et al. | 367/149 |
| 2007/0108874 A1* | 5/2007 | Okazaki et al. | 310/348 |
| 2007/0287912 A1* | 12/2007 | Khuri-Yakub et al. | 600/439 |
| 2008/0212407 A1* | 9/2008 | Caliano et al. | 367/140 |
| 2009/0015108 A1* | 1/2009 | Ishimasa et al. | 310/353 |

FOREIGN PATENT DOCUMENTS

| | | |
|---|---|---|
| DE | 10 2005 049 631 | 6/2006 |
| DE | 10 2006 021 492 | 11/2007 |
| DE | 10 2007 057 124 | 7/2008 |
| DE | 10 2008 018 110 | 10/2008 |
| EP | 17 40 014 | 1/2007 |

OTHER PUBLICATIONS

Wygant, E.O., et al., 50 kHz Capacitive Micromachined Ultrasonic Trsducers for Generation of Highly Directional Sounds With Paramaetric Arrays. IEEE Trans. Ultrasonics, Ferroeledtircs and Frequency Control, 2009, No. 1. p. 193-203.

Yoshiro Tomikawa et al., "Wide Band Ultrasonic Transducer Using Tapered Piezoelectric Ceramics for Non-Destructive Inspection", Japanese Journal of Applied Physics, Bd. 23, Nr. 23-1, Jan. 1, 1983 pp. 113-115.

* cited by examiner

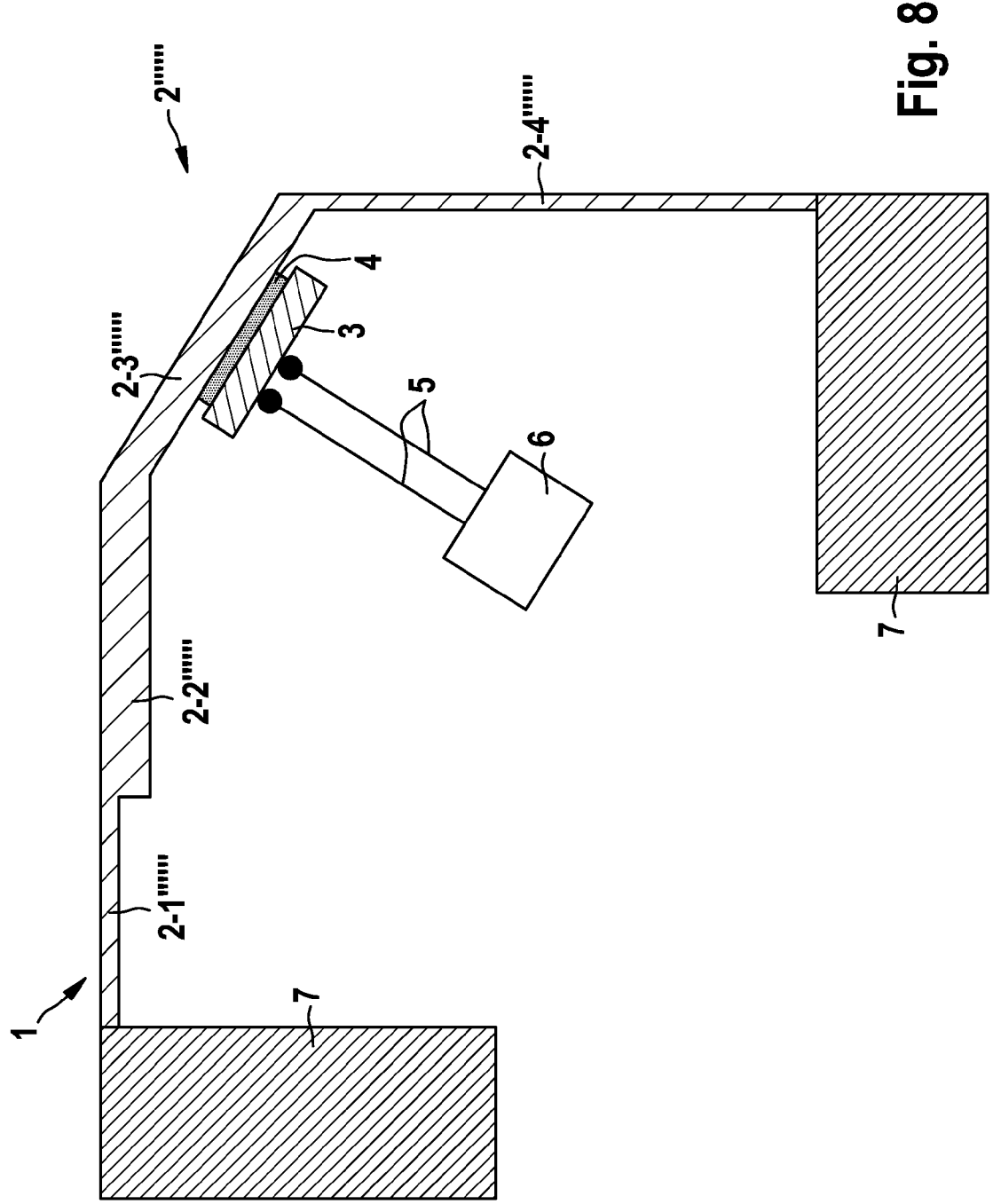

METHOD FOR CONTROLLING AN ULTRASONIC SENSOR AND ULTRASONIC SENSOR

BACKGROUND OF THE INVENTION

1. Field of the Invention

The present invention relates to a method for controlling an ultrasonic sensor, and to an ultrasonic sensor.

2. Description of the Related Art

Ultrasonic sensors have been used for decades in vehicles for surrounding-area detection. In this context, the measuring systems are based on an echo method, in which a transmitted signal is reflected by an obstacle and echoed back to the vehicle in the form of an echo signal. The distance of the obstacle from the vehicle is then determined with the aid of the measured echo delay time. This information is then used for many different driver assistance systems, such as parking assistance systems or also blind spot monitoring systems. In this context, the ultrasonic sensors are mostly implemented in the form of an ultrasonic transducer, which allows switching-over between transmit mode and receive mode.

Conventional ultrasonic sensors include a diaphragm, which, in transmit mode, converts mechanical vibrations in the ultrasonic range into pressure fluctuations of the air surrounding the vehicle, and an electromechanical transducer, e.g., in the form of a piezoelectric resonator, which is coupled to the diaphragm, e.g., with the aid of an adhesive bond, and, in transmit mode, converts electrical signals into vibrations in the ultrasonic range. In order to give the radiation of the diaphragm a direction, it is normally mounted to a chassis, which, in contrast to the diaphragm, is supposed to have negligible vibrational amplitudes.

As a rule, ultrasonic sensors are operated in the range of their respective resonant frequency, which results from the resonance characteristics of the respective diaphragm and the respective transducer, since particularly efficient conversion of electrical oscillation power into mechanical vibration power, and vice versa, is present there.

A method for adjusting the resonant frequency of a vibrating section of a housing of an ultrasonic sensor, in which the resonant frequency of the vibrating section is measured and compared to a previously established threshold value of a setpoint resonant frequency, is known from published German patent application document DE 10 2006 021 492 A1. In light of the comparison, the resonant frequency of the vibrating section is adjusted by appropriately removing or applying material.

BRIEF SUMMARY OF THE INVENTION

The present invention provides an ultrasonic sensor, which has a diaphragm including at least two partial regions for emitting and/or receiving ultrasonic signals, where the two partial regions possess different resonance characteristics, and which has at least one electromechanical transducer, which is coupled to the diaphragm, and to which a control signal having at least two different control signal frequencies may be applied. In this context, a first control signal frequency is in the range of a resonant frequency of a first partial region of the diaphragm, and a second control signal frequency is in the range of a resonant frequency of a second partial region of the diaphragm. In this instance, the different resonance characteristics are advantageously produced, using different thicknesses of the diaphragm.

In addition, the present invention provides a method for controlling an ultrasonic sensor, which has a diaphragm including at least two partial regions having different resonance characteristics, and which has at least one electromechanical transducer coupled to the diaphragm, where a control signal having at least two different control signal frequencies is applied to the electromechanical transducer. In this context, a first control signal frequency is in the range of a resonant frequency of a first partial region of the diaphragm, and a second control signal frequency is in the range of a resonant frequency of a second partial region of the diaphragm.

In this context, here and in the following, the wording "resonant frequency of a partial region" refers to the resonant frequency, which results from the resonance characteristics of the diaphragm and the electromechanical transducer(s) coupled to it.

The present invention is based on the fundamental idea of designing and positioning the diaphragm and the electromechanical transducer(s) in such a manner, and controlling the electromechanical transducer(s) in such a manner, that the ultrasonic sensor has more than one resonant frequency, at which electrical oscillation power is converted particularly effectively into acoustic vibration power, or vice versa. By using ultrasonic signals having different frequencies, it is possible to improve the ultrasonic-based, surrounding-area detection of a vehicle with regard to its reliability, range and/or response speed. Thus, for example, using multifrequency or broadband modulation, echo signals, which are based on transmitted signals that were emitted a relatively long time ago (long-delay echoes), and/or external or interference signals, may be distinguished in a markedly more reliable manner from echoes, which are the result of signals emitted a short time ago. In this context, signals of both the reference vehicle and another vehicle and/or of devices, which are situated in the surrounding area of the vehicle, may be taken into consideration.

According to one specific embodiment of the present invention, the diaphragm may be shaped so that the diaphragm thickness changes in a stepped manner. As an alternative to that, a continuous change in the diaphragm thickness may also be provided, which results in a wide spectrum of usable signal frequencies.

The diaphragm may be formed to be symmetric or asymmetric as a function of the specific application case and the specific problem definition, which means that symmetric or asymmetric emitting and/or receiving directions result accordingly.

The present invention's idea of a multifrequency ultrasonic sensor may also be implemented by an ultrasonic sensor, which has a diaphragm including at least two partial regions for emitting and/or receiving ultrasonic signals, and has at least two electromechanical transducers that are coupled to the diaphragm and have different resonance characteristics, which may be achieved, for example, by different geometric dimensions of the transducers. In this context, a control signal may be applied to each transducer, the control signals being independent of each other and each including at least one control signal frequency, which is in the range of a resonant frequency of the specific partial region of the diaphragm.

In order to obtain symmetric or asymmetric emitting and/or receiving directions, the transducers may be correspondingly coupled to the diaphragm in a symmetric or asymmetric manner.

Corresponding to such an ultrasonic sensor, the present invention also provides a method for controlling an ultrasonic sensor, which has a diaphragm including at least two partial regions for emitting and/or receiving ultrasonic signals, and has at least two electromechanical transducers in each of the partial regions, the electromechanical transducers being coupled to the diaphragm and having different resonance characteristics. According to the present invention, a control signal is applied to each transducer, the control signals being independent of each other and each including at least one control signal frequency, which is in the range of a resonant frequency of the specific partial region of the diaphragm.

An ultrasonic sensor having a diaphragm and at least one electromagnetic transducer, which is coupled to the diaphragm and has at least three electrodes, is suited for implementing the fundamental inventive idea, the transducer having different resonance characteristics as a function of the control of the electrodes. This embodiment has the advantage that a single electromechanical transducer in conjunction with a "classic" diaphragm is already sufficient for implementing a multifrequency ultrasonic sensor.

Accordingly, the present invention also provides a method for controlling an ultrasonic sensor having a diaphragm and at least one electromechanical transducer coupled to the diaphragm, the transducer having at least three electrodes, and a first electrode pair being controlled in order to emit an ultrasonic signal having a first transmitted-signal frequency, and a second electrode pair being controlled in order to emit an ultrasonic signal having a second transmitted-signal frequency.

A further specific embodiment of the present invention provides that a preferred transmission direction of ultrasonic signals be set with the aid of control signal frequencies of the control signal of the transducer. To that end, the signal frequencies are set in such a manner, that either the conversion of the electrical oscillation power into acoustic vibrational power (transmit mode) is carried out at a resonant frequency, and therefore, particularly effectively, or that the conversion of the acoustic vibrational power into electrical oscillation power (receive mode) is carried out at a resonant frequency, and therefore, particularly effectively. Transmitting and receiving frequencies may deviate from one another, for example, due to Doppler effects.

BRIEF DESCRIPTION OF THE DRAWINGS

FIG. 8 shows a schematic representation of an ultrasonic sensor according to a sixth specific embodiment of the present invention.

DETAILED DESCRIPTION OF THE INVENTION

Figure 1:
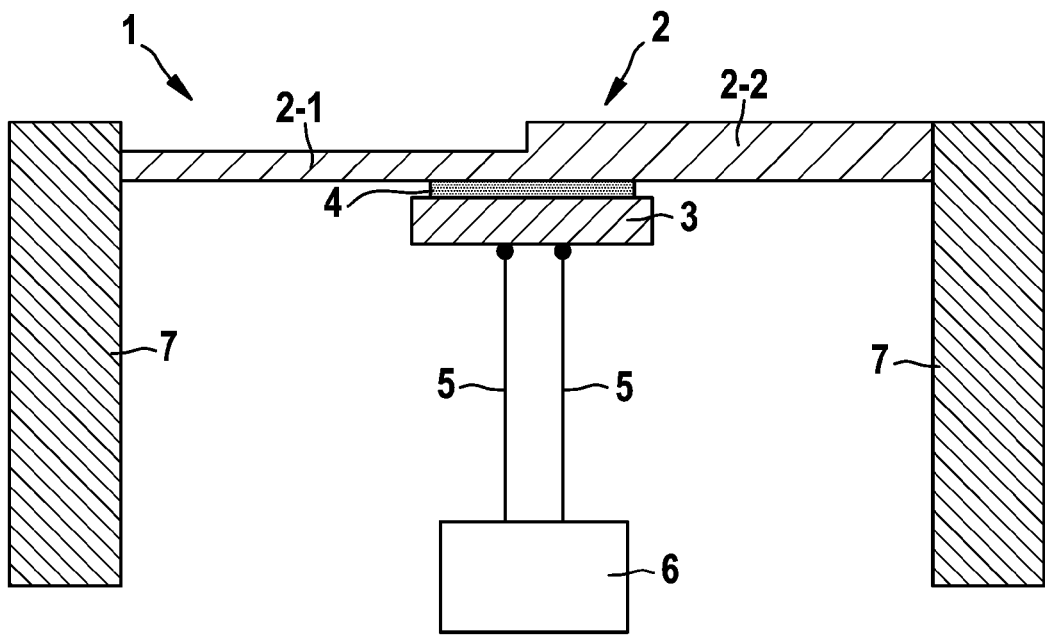
FIG. 1 shows a schematic sectional view of an ultrasonic sensor according to a first specific embodiment of the present invention.

In the figures, like or functionally equivalent components are each denoted by the same reference numeral.

FIG. 1 schematically shows an ultrasonic sensor 1 according to a first specific embodiment of the present invention. An electromechanical transducer in the form of a piezoelectric resonator 3 is attached to a diaphragm 2 with the aid of an adhesive layer 4 and coupled to diaphragm 2 in this manner. A control signal, as a result of which piezoelectric resonator 3 is set into mechanical vibrations, is applied to piezoelectric resonator 3 by a control unit 6 via electrical leads 5. These vibrations are transmitted through adhesive layer 4 to diaphragm 2. Diaphragm 2 produces pressure fluctuations in the air in front of it, through which sonic waves are emitted. In order to give the emitted sonic waves a direction, the diaphragm is attached to a chassis 7, which, in contrast to the diaphragm, has negligible vibrational amplitudes. In the case of receiving sonic waves, the signal path correspondingly runs in reverse, that is, incident acoustic waves are ultimately converted into electrical signals.

Diaphragm 2 includes two partial regions 2-1 and 2-2, which have different thicknesses or material strengths that account for different resonance characteristics of the two partial regions. In the specific embodiment shown, the transition between the two partial regions 2-1 and 2-2 is constructed to be stepped, so that in each of the two partial regions 2-1 and 2-2, a resonant frequency results at which electrical oscillation power is converted particularly effectively into acoustic vibrational power, or vice versa. By applying a control signal, which includes at least these two resonant frequencies or at least two frequencies in the range of these resonant frequencies, the ultrasonic sensor may be operated simultaneously at two resonant frequencies. In this context, a preferred transmission direction of ultrasonic sensor 1, i.e., transmitting or receiving, is set with the aid of the signal frequencies of the control signal. To that end, the signal frequency is either selected to be identical to the resonant frequency, so that the conversion of the electrical oscillation power into the mechanical vibrational power and, therefore, the transmit mode, is optimum; or a signal frequency in the range of the resonant frequency is selected, which results in a possible echo signal having exactly the resonant frequency and, therefore, an optimum conversion of the mechanical vibrational power to the electrical oscillation power (receive mode). In this context, frequency differences between the transmitted signal and the echo signal may be due to the Doppler effect, for example.

In the exemplary embodiment shown, piezoelectric resonator 3 is situated below the transition region between partial regions 2-1 and 2-1 of diaphragm 2. However, this is not essential to the use of the present invention. It is also sufficient for the partial regions of the diaphragm, which have different resonance characteristics, to be situated in a region around an electromechanical transducer.

Figure 2:
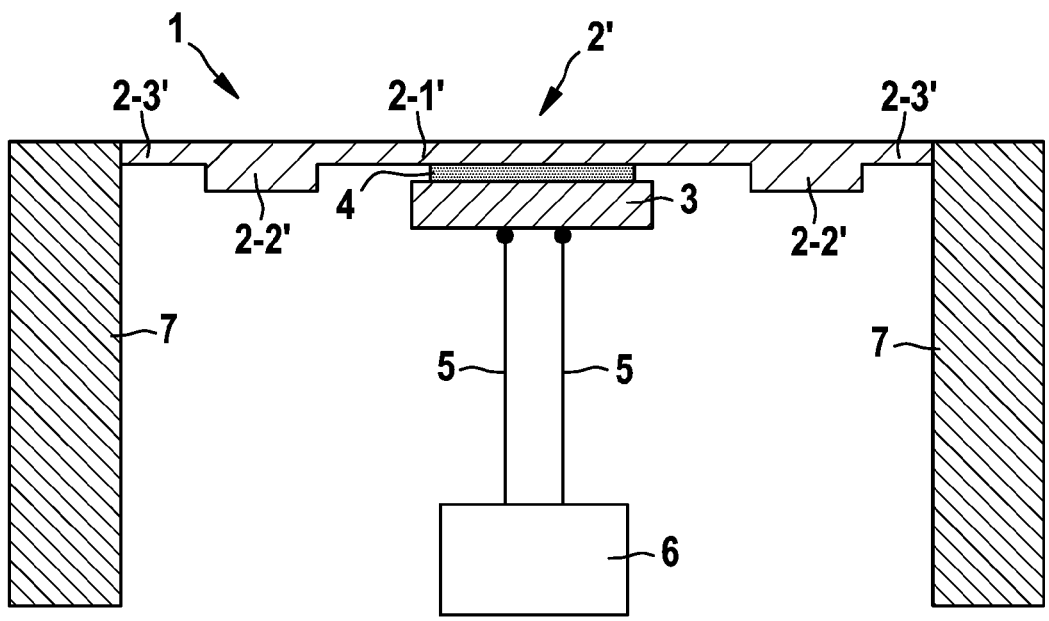
FIG. 2 shows a schematic sectional view of an ultrasonic sensor according to a second specific embodiment of the present invention.

Such a specific embodiment is illustrated in FIG. 2 This specific embodiment mainly differs from the specific embodiment represented in FIG. 1 in that in a first partial region 2-1' over piezoelectric resonator 3, diaphragm 2' has a constant thickness, but that second partial regions 2-2' having increased thickness or material strength and, consequently, a changed resonance characteristic, are situated on both sides of piezoelectric resonator 3. In third partial regions 2-3', via which diaphragm 2' is attached to chassis 7, the diaphragm again has the thickness of first partial region 2-1' or, alternatively, a further, arbitrary thickness, as well. In order to provide decoupling between diaphragm 2 and chassis 7 that is as effective as possible, it is advantageous to design the edge regions of diaphragm 2', which are directly adjacent to chassis 7, to be as thin as possible. This rule is also applicable to other exemplary embodiments, which means that in these specific embodiments, "thinned" edge regions of diaphragm 2 may also be provided. However, it should be pointed out that edge regions constructed in such a manner are not used for emitting or receiving an ultrasonic signal, but solely for decoupling from chassis 7.

The specific embodiment according to FIG. 2 further differs from the one of FIG. 2 in that the stepped transitions between the individual partial regions are positioned symmetrically, and therefore, diaphragm 2' is formed symmetrically. Symmetric or asymmetric positioning may allow symmetric or asymmetric emitting or receiving directions to be achieved in a corresponding manner.

Figure 3:
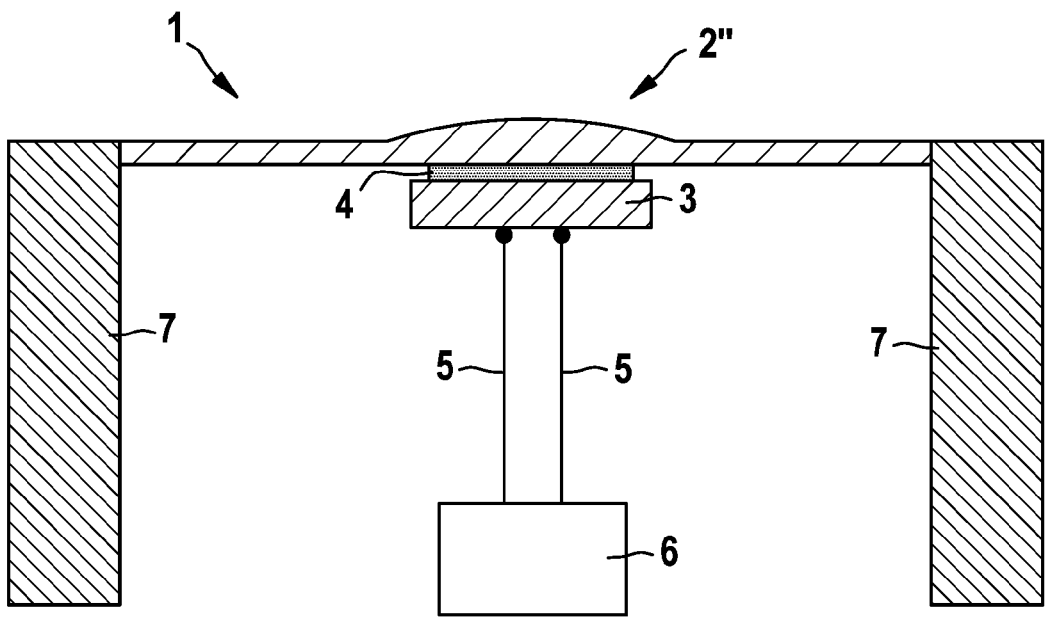
FIG. 3 shows a schematic sectional view of an ultrasonic sensor according to a third specific embodiment of the present invention.
Figure 4:
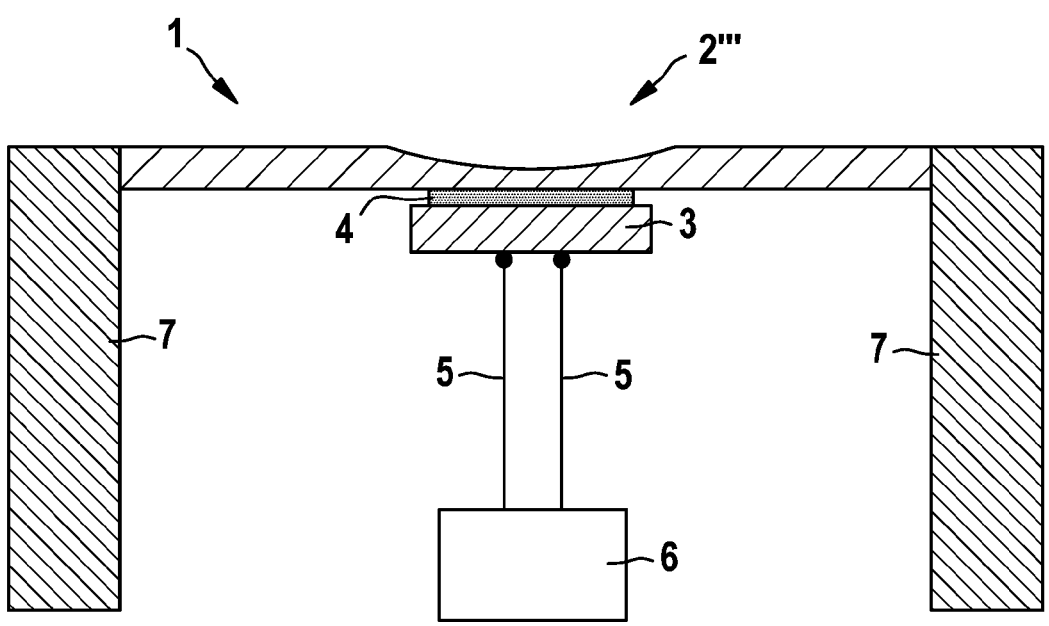
FIG. 4 shows a schematic sectional view of an ultrasonic sensor according to a fourth specific embodiment of the present invention.

FIGS. 3 and 4 show further specific embodiments of ultrasonic sensors according to the present invention. These differ from the specific embodiment represented in FIG. 1 in that the thicknesses of diaphragms 2" (see FIG. 3) and 2''' (see FIG. 4) do not change in a stepped manner, but continuously. In particular, the diaphragm 2" according to FIG. 3 is convex, and the diaphragm 2''' according to FIG. 4 is concave. In this manner, a multitude of partial regions of diaphragm 2", 2''' having different mechanical properties is formed, as it were, which results in a wide spectrum of usable resonant frequencies.

Figure 5:
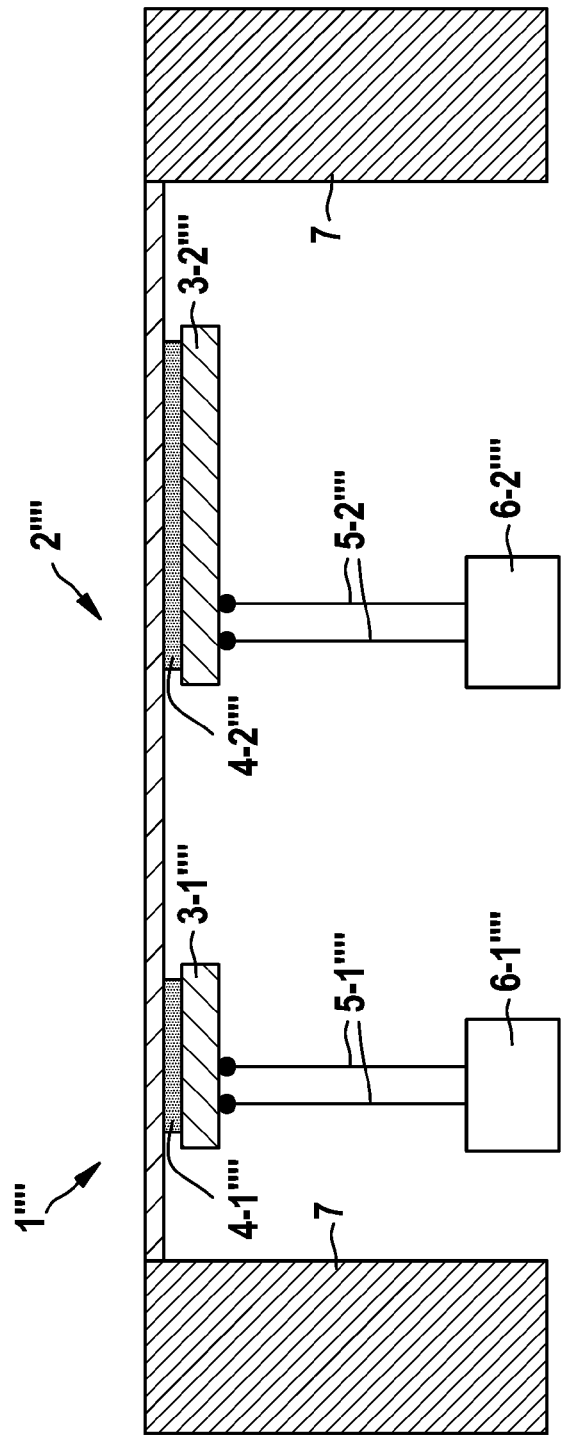
FIG. 5 shows a schematic sectional view of an ultrasonic sensor according to a fifth specific embodiment of the present invention.

An alternative specific embodiment of an ultrasonic sensor 1'''' according to the present invention is represented in FIG. 5. In this context, on a "conventional" diaphragm 2'''' having a constant thickness, two electromechanical transducers in the form of piezoelectric resonators 3-1'''' and 3-2'''' are attached to partial regions of diaphragm 2'''' with the aid of adhesive layers 4-1'''' and 4-2'''', respectively, and, in this manner, are coupled to diaphragm 2''''. In this instance, the two piezoelectric resonators 3-1'''' and 3-2'''' have different geometric dimensions and also different resonance characteristics caused by them. By applying a control signal in each instance, in which case the control signals of the two piezoelectric resonators 3-1'''' and 3-2'''' are independent of one another and each include at least one control signal frequency, which is in the range of a resonant frequency of the respective partial region of the diaphragm, this set-up also produces an ultrasonic sensor, which is operable at two resonant frequencies. In the specific embodiment shown, the two control signals are generated by two separate control units 6-1'''' and 6-2'''' and applied to piezoelectric resonators 3-1'''' and 3-2'''', respectively, via electrical leads 5-1'''' and 5-2'''', respectively. As an alternative to that, the control signals may also be generated by a common control unit. Due to the asymmetric set-up, asymmetric emitting and/or receiving characteristics are obtained in a simple manner. Of course, more than two piezoelectric resonators may also be provided, which may also be positioned symmetrically, if necessary.

Figure 6:
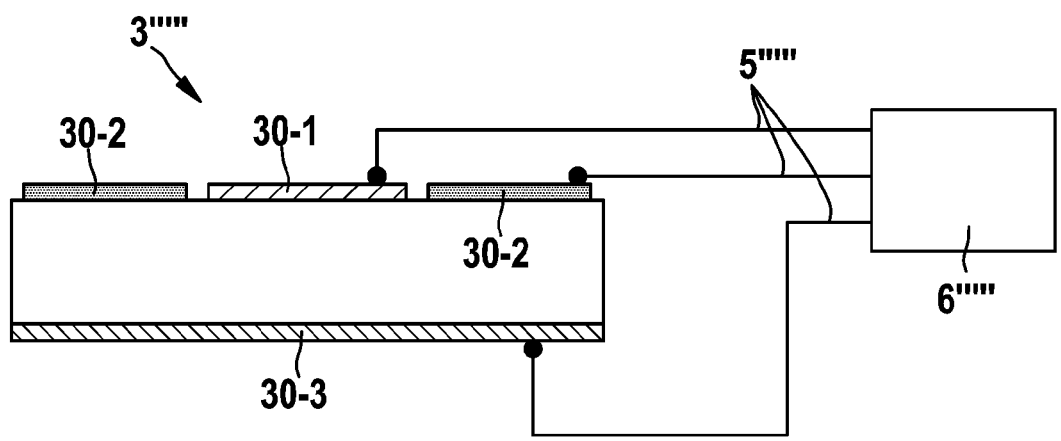
FIG. 6 shows a schematic sectional view of an electromechanical transducer of the present invention, having three electrodes.
Figure 7:
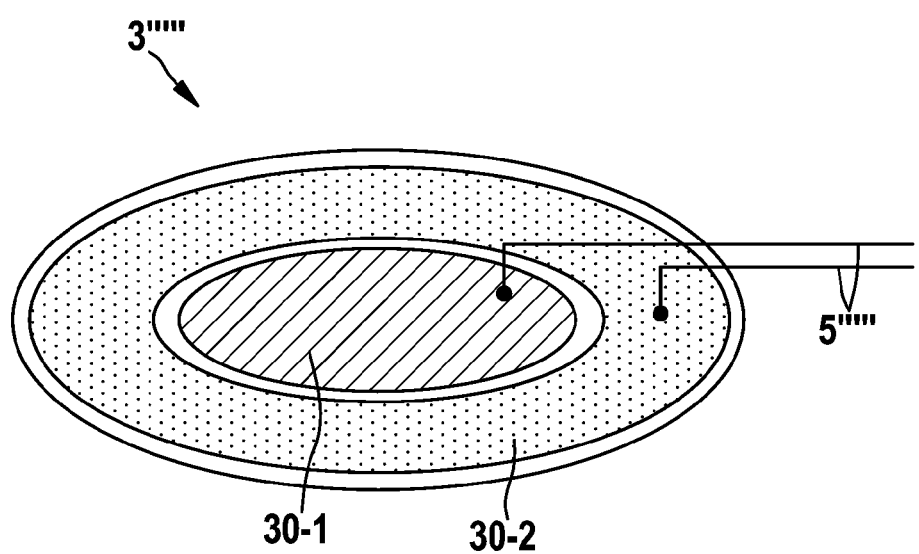
FIG. 7 shows a top view of a schematic representation of an electromechanical transducer according to the present invention, having three electrodes.

A further specific embodiment of the present invention (see FIGS. 6 and 7) provides for the use of a piezoelectric resonator 3''''', which has three electrodes 30-1, 30-2 and 30-3. In this context, a first electrode 30-1 is situated in the central upper region of piezoelectric resonator 3''''', a second electrode 30-2 is situated in the edge region of the upper side of piezoelectric resonator 3''''' and a third electrode 30-3 is situated on the lower side of piezoelectric resonator 3'''''. All three electrodes 30-1, 30-2, and 30-3 may be controlled by a control unit 6 via corresponding electrical leads 5'''''. Due to the positioning and the shape of electrodes 30-1, 30-2 and 30-3, in the case of controlling a first electrode pair made up of electrodes 30-1 and 30-3, resonance characteristics and also directivity characteristics are produced, which are different from the case in which a second electrode pair made up of electrodes 30-2, 30-3 is controlled. If such a piezoelectric resonator 3''''' is coupled to a diaphragm, it is even possible to operate the ultrasonic sensor at different resonant frequencies in the case of a "conventional" diaphragm having a constant thickness.

FIG. 8 shows a further specific embodiment of the present invention, in which a diaphragm 2'''''' is provided that includes four partial regions 2-1'''''', 2-2'''''', 2-3'''''' and 2-4''''''. These are formed in such a manner, that a second partial region 2-2'''''' having a second thickness is rectilinearly contiguous to a first partial region 2-1'''''', which is attached to a left-hand portion of chassis 7. A third partial region 2-3'''''' having a third thickness connects to second partial region 2-2'''''' at a predefined angle; a fourth partial region 2-4'''''', which has a fourth thickness and is attached to the right-hand portion of chassis 7, finally connecting to the third partial region at a further, predefined angle. In the area of third partial region 2-3'''''', piezoelectric resonator 3 is attached to diaphragm 2'''' with the aid of adhesive layer 4 and, therefore, coupled to it. In this specific embodiment, the different thicknesses of the individual partial regions of diaphragm 2'''''' also produce different resonance characteristics, which, by suitable controlling, may be used for implementing a multifrequency ultrasonic sensor. In addition, various preferred orientations of the transmitted or received signals may be obtained, using the three-dimensional shape of diaphragm 2''''''.

In addition to the specific embodiments illustrated and described, numerous other specific embodiments of the present invention are conceivable, which result, in particular, from combinations of the specific embodiments mentioned.

What is claimed is:

1. An ultrasonic sensor, comprising:
   a diaphragm which has at least two partial regions for at least one of emitting and receiving ultrasonic signals, the two partial regions having different resonance characteristics;
   a chassis attached to the diaphragm, the chassis having negligible vibrational amplitudes; and
   at least one electromechanical transducer coupled to the diaphragm, wherein a control signal having at least two different control signal frequencies is applied to the electromechanical transducer, a first control signal frequency being in the range of a resonant frequency of a first partial region of the diaphragm, and a second control signal frequency being in the range of a resonant frequency of a second partial region of the diaphragm;
   wherein the electromechanical transducer is attached to the diaphragm by an adhesive layer, and is attached to a control unit via electrical leads.

2. The ultrasonic sensor as recited in claim 1, wherein the different resonance characteristics are produced by different thicknesses of the at least two partial regions of the diaphragm.

3. The ultrasonic sensor as recited in claim 2, wherein the thickness of the diaphragm changes in a stepped manner between the at least two partial regions.

4. The ultrasonic sensor as recited in claim 2, wherein the thickness of the diaphragm changes continuously at least in a transition area between the first partial region and the second partial region.

5. The ultrasonic sensor as recited in claim 4, wherein the diaphragm is configured symmetrically.

6. The ultrasonic sensor as recited in claim 2, wherein the diaphragm is configured asymmetrically.

7. The ultrasonic sensor as recited in claim 1, wherein the chassis is decouplably attached to the diaphragm.

8. The ultrasonic sensor as recited in claim 1, wherein an edge region of the diaphragm directly adjacent to the chassis is thinner than the two partial regions of the diaphragm.

9. A method for controlling an ultrasonic sensor having a diaphragm which includes at least two partial regions possessing different resonance characteristics, and at least one electromechanical transducer being coupled to the diaphragm, the method comprising:
- applying a control signal having at least two different control signal frequencies to the electromechanical transducer, a first control signal frequency being in the range of a resonant frequency of a first partial region of the diaphragm, and a second control signal frequency being in the range of a resonant frequency of a second partial region of the diaphragm;
- wherein a chassis is attached to the diaphragm, the chassis having negligible vibrational amplitudes; and
- wherein the electromechanical transducer is attached to the diaphragm by an adhesive layer, and is attached to a control unit via electrical leads.

* * * * *